United States Patent
Lim et al.

(10) Patent No.: US 10,082,487 B2
(45) Date of Patent: Sep. 25, 2018

(54) APPARATUS AND METHOD FOR ULTRASONIC DETECTION TO DETECT FLAWS OF STEEL PLATE

(71) Applicant: POSCO, Pohang-si, Gyeongsangbuk-do (KR)

(72) Inventors: Choong Soo Lim, Pohang-si (KR); Myung Sik Chun, Pohang-si (KR); Hyeong Jun Huh, Suncheon-si (KR); Boong Ho Son, Pohang-si (KR)

(73) Assignee: POSCO, Pohang-si, Gyeongsangbuk-do (KR)

( * ) Notice: Subject to any disclaimer, the term of this patent is extended or adjusted under 35 U.S.C. 154(b) by 155 days.

(21) Appl. No.: 15/107,827

(22) PCT Filed: Dec. 26, 2013

(86) PCT No.: PCT/KR2013/012207
§ 371 (c)(1),
(2) Date: Jun. 23, 2016

(87) PCT Pub. No.: WO2015/099229
PCT Pub. Date: Jul. 2, 2015

(65) Prior Publication Data
US 2016/0320345 A1    Nov. 3, 2016

(30) Foreign Application Priority Data

Dec. 23, 2013    (KR) .................. 10-2013-0161414
Dec. 26, 2013    (KR) .................. 10-2013-0163517

(51) Int. Cl.
*G01N 29/28*    (2006.01)
*G01N 29/04*    (2006.01)
*G01H 3/00*    (2006.01)

(52) U.S. Cl.
CPC ............. *G01N 29/043* (2013.01); *G01H 3/00* (2013.01); *G01N 29/28* (2013.01);
(Continued)

(58) Field of Classification Search
CPC ...... G01N 29/04; G01N 29/28; G01N 29/228; G01N 2291/0234; G01N 2291/044; G01N 2291/2632
(Continued)

(56) References Cited

U.S. PATENT DOCUMENTS 2,751,783 A * 6/1956 Erdman ................. G10K 11/02
                                                          73/634
3,908,446 A * 9/1975 Mruk ..................... G01B 17/02
                                                          73/620
(Continued)

FOREIGN PATENT DOCUMENTS

CN    1849510 A    10/2006
JP    46-10640    4/1971
(Continued)

OTHER PUBLICATIONS

Extended European Search Report dated Jun. 8, 2017 issued in European Patent Application No. 13900485.7.
(Continued)

*Primary Examiner* — Manish S Shah
*Assistant Examiner* — Rose M Miller
(74) *Attorney, Agent, or Firm* — McDermott Will & Emery LLP

(57) ABSTRACT

An apparatus and a method for ultrasonic detection are provided. The apparatus includes an injection nozzle which is installed below a steel plate being transported and forms a medium column by jet a medium toward the steel plate, an ultrasonic probe which is installed in the injection nozzle and transmits and receives ultrasonic waves for detecting
(Continued)

flaws in the steel plate through the medium column, and a medium circulation unit which reclaims the medium which falls from the medium column and circulates the reclaimed medium to the injection nozzle.

11 Claims, 8 Drawing Sheets

(52) U.S. Cl.
CPC .......... *G01N 2291/0234* (2013.01); *G01N 2291/044* (2013.01); *G01N 2291/2632* (2013.01)

(58) Field of Classification Search
USPC .................................................. 73/627, 644
See application file for complete search history.

(56) References Cited

U.S. PATENT DOCUMENTS

| | | | |
|---|---|---|---|
| 4,558,598 A | | 12/1985 | Young |
| 4,976,149 A | * | 12/1990 | Ichikawa ............ B21B 38/12 367/104 |
| 6,266,983 B1 | | 7/2001 | Takada et al. |
| 2004/0200284 A1 | * | 10/2004 | Kessier ............... G01N 29/06 73/603 |

FOREIGN PATENT DOCUMENTS

| | | |
|---|---|---|
| JP | 59-090047 A | 5/1984 |
| JP | 60-198452 A | 10/1985 |
| JP | 05-172799 A | 7/1993 |
| JP | 7-113795 A | 5/1995 |
| JP | 07-318539 A | 12/1995 |
| JP | 3097253 B2 | 8/2000 |
| JP | 3565134 B2 | 9/2004 |
| JP | 2004-286509 A | 10/2004 |
| JP | 2008-180523 A | 8/2008 |
| JP | 2010-66168 A | 3/2010 |
| JP | 5172032 B1 | 3/2013 |
| JP | 2013-156187 A | 8/2013 |
| KR | 10-0203514 B1 | 6/1999 |
| KR | 10-0719635 B1 | 5/2007 |
| KR | 10-1276764 A | 6/2012 |
| KR | 10-2013-0058946 A | 6/2013 |
| WO | 2004/092779 A2 | 10/2004 |

OTHER PUBLICATIONS

Japanese Office Action dated May 9, 2017 issued in Japanese Patent Application No. 2016-560320 (with English translation).
International Search Report issued in corresponding International Patent Application No. PCT/KR2013/012207, dated Sep. 23, 2014; 4 pages with English translation.
Chinese Office Action dated Feb. 23, 2018 issued in Chinese Patent Application No. 2013800818269 (with English translation).
Korean Office Action issued in Korean Patent Application No. 10-2013-0161414, dated May 7, 2015; 5 pages with English translation.
Korean Office Action issued in Korean Patent Application No. 10-2013-0163517, dated May 27, 2015; 5 pages with English translation.
Decision to Refuse Patent issued in Korean Patent Application No. 10-2013-0161414, dated Aug. 21, 2015; 3 pages with English translation.
Decision to Refuse Patent issued in Korean Patent Application No. 10-2013-0163517, dated Aug. 21, 2015; 3 pages with English translation.
Decision to Refuse Patent issued in Korean Patent Application No. 10-2013-0161414, dated Oct. 2, 2015; 3 pages with English translation.

* cited by examiner

APPARATUS AND METHOD FOR ULTRASONIC DETECTION TO DETECT FLAWS OF STEEL PLATE

CROSS-REFERENCE TO RELATED APPLICATION

This application is the U.S. National Phase under 35 U.S.C. § 371 of International Patent Application No. PCT/KR2013/012207, filed on Dec. 26, 2013, which in turn claims the benefit and priority from Korean Patent Application Numbers 10-2013-0161414, filed Dec. 23, 2013 and 10-2013-0163517, filed Dec. 26, 2013, the subject matters of which are hereby incorporated by reference.

BACKGROUND

1. Field of the Invention

The present invention relates to an apparatus and a method for ultrasonic detection of internal flaws of a manufactured steel plate.

2. Discussion of Related Art

In a thick plate factory, ultrasonic detection is used in a quality control process before product shipment in order to detect internal flaws in manufactured steel plates. The ultrasonic detection is a method for determining whether flaws including cracks, intervening materials, segregations, etc. are present in steel plates by transmitting ultrasonic waves to the steel plates and receiving as well as analyzing ultrasonic waves reflected by the steel plates.

The ultrasonic detection may be divided into contact type detection methods and noncontact type detection methods depending on whether or not an ultrasonic probe contacts a steel plate surface.

In the case of the contact type detection methods, misdetections frequently occur because of noise occurrences due to surface conditions and shapes of a steel plate, and a deterioration of the detection performance and a reduction of the life of an ultrasonic probe occur due to abrasions of the detection surface of the probe due to frictions between the ultrasonic probe and the steel plate.

To overcome such limitations of the contact type detection methods, various noncontact type detection methods are being considered. In the case of the noncontact detection methods, a contact medium is necessary to transfer ultrasonic energy oscillated by an ultrasonic probe, and as a representative medium, there is water with excellent ultrasonic wave transmission efficiency.

FIG. 1 illustrates a submersible ultrasonic detection method among noncontact ultrasonic detection methods for detecting flaws in steel plates.

As shown in FIG. 1, a steel plate 3 is submerged in a bath 1 filled with water, and ultrasonic detection is performed above the steel plate 3 using a submersion type ultrasonic probe 2. Accordingly, since the entire steel plate 3 is under water, even when the ultrasonic probe 2 moves, there is an advantage where it is possible to maintain constant efficiency of transmitting and receiving ultrasonic waves.

However, in the case of applying the submersing ultrasonic detection method to a process of producing thick plates in a steel mill, a bath 1 with a large size for submersing the steel plate 3 transported by a roll 4 and a vertical movement device 5 for vertically moving the steel plate 3 in the bath 1 are necessary. For this, a large-scale construction work for structurally changing the facilities of the steel mill is needed.

FIG. 2 illustrates a water jet method among methods for detecting flaws in steel plates using noncontact ultrasonic detection methods.

The water jet method is a method of spraying water to a steel plate to provide a water path and transmitting and receiving ultrasonic waves through the water path. Since it is unnecessary to deposit an entire steel plate in a bath, the waterjet method described above has the advantages of more easily providing for facilities than the submersible ultrasonic detection method.

Referring to FIG. 2, water storage rolls 6 are installed in the front and rear of an ultrasonic probe 2 along a longitudinal direction of a steel plate 3, water is supplied through a nozzle 7 and a water supply pipe 8 to store a certain amount of water, and then ultrasonic detection is performed above the steel plate 3. In this case, even when a steel plate is moved, there is an advantage that the ultrasonic detection is still possible through rotation of the water storage rolls 6.

However, even in such a case, since it is impossible to store water when a front end and a rear end of the steel plate 3 enter the detection region, it is impossible to detect a corresponding portion. Also, when the width of a steel plate changes, there is a problem where stored water falls through both edge portions of the steel plate.

SUMMARY OF THE INVENTION

The present invention is directed to providing an apparatus and a method for ultrasonic detection in which a medium (water) column is formed below a steel plate, and ultrasonic waves are transmitted and received, thereby stably transmitting and receiving ultrasonic waves and reclaiming and reusing the medium.

Additional aspects will be set forth in part in the description which follows and, in part, will be apparent from the description, or may be learned by practice of the presented embodiments.

One aspect of the present invention provides an ultrasonic detection apparatus including an injection nozzle which is installed below a steel plate being transported and forms a medium column by jetting a medium toward the steel plate, an ultrasonic probe which is installed in the injection nozzle and transmits and receives ultrasonic waves for detecting flaws in the steel plate through the medium column, and a medium circulation unit which reclaims the medium falling from the medium column and circulates the reclaimed medium to the injection nozzle.

The medium circulation unit may include a medium plate which is installed on an outer perimeter of the injection nozzle and receives the medium which falls from the medium column, a reclaiming pipe which is connected to the medium plate and reclaims the medium in the medium plate, and a supply pipe for supplying the medium in the reclaiming pipe to the injection nozzle.

A filter for filtering the medium discharged from the medium plate may be installed at the reclaiming pipe.

The ultrasonic detection apparatus may further include a jet pressure control unit for supplying a jet pressure to the injection nozzle and controlling the jet pressure of the injection nozzle.

The jet pressure control unit may be installed between the supply pipe connected to the injection nozzle and the reclaiming pipe connected to the medium plate installed on the outer perimeter of the injection nozzle.

The jet pressure control unit may be a circulation pump.

The jet pressure control unit may include a medium chamber for containing the medium which falls from the medium column and is reclaimed and supplying the contained medium again to the injection nozzle and a surface level adjustor which adjusts the surface level of the medium contained in the medium chamber to control the jet pressure of the injection nozzle.

The surface level adjustor may include a level sensor which senses the surface level of the medium contained in the medium chamber, a first pipe for supplying the medium to the medium chamber, a second pipe for discharging the medium from the medium chamber, and a control unit which is connected to the first and second pipes and controls flow rates of the medium in the first and second pipes such that the surface level of the medium has a certain value based on a value sensed the level sensor.

The control unit may include a supply chamber which is connected between the first and second pipes and contains the medium, a supply pump installed at one of the first pipe and the second pipe, first and second control valves installed at the first and second pipes, respectively, and a controller which controls the first and second control valves based on the value sensed by the level sensor.

The jet pressure control unit may include a medium chamber for containing the medium which falls from the medium column and is reclaimed and supplying the contained medium again to the injection nozzle and a chamber height adjustor which adjusts a height of the medium chamber to control the jet pressure of the injection nozzle.

The chamber height adjustor may include a driving portion which drives the medium chamber to move in the vertical direction and a controller which controls an operation of the driving portion according to an input signal.

A plurality of the ultrasonic probes may be arranged in the width direction of the steel plate, and the injection nozzle may be configured to accommodate a probe array formed by the plurality of ultrasonic probes. Here, the probe array may have a length that is greater than or equal to the width of the steel plate.

Another aspect of the present invention provides an ultrasonic detection method including transporting a steel plate, forming a medium column by jetting a medium to the steel plate through an injection nozzle installed below the steel plate, detecting internal flaws of the steel plate by operating an ultrasonic probe disposed in the injection nozzle to transmit and receive ultrasonic waves through the medium column, and reclaiming the medium which falls from the medium column and supplying the reclaimed medium again to the injection nozzle.

The medium column may be formed to have a height greater than the distance between a jet hole of the injection nozzle and a lower surface of the steel plate while the medium is being jetted in such a way that an upper portion of the medium column is to be better closely attached to the lower surface of the steel plate.

BRIEF DESCRIPTION OF THE DRAWINGS

The above and other objects, features and advantages of the present invention will become more apparent to those of ordinary skill in the art by describing in detail exemplary embodiments thereof with reference to the attached drawings, in which.

DETAILED DESCRIPTION OF EXEMPLARY EMBODIMENTS

Hereinafter, an apparatus and a method for ultrasonic detection to detect flaws of a steel plate according to an exemplary embodiment of the present invention will be described in detail with reference to the attached drawings.

Figure 1:
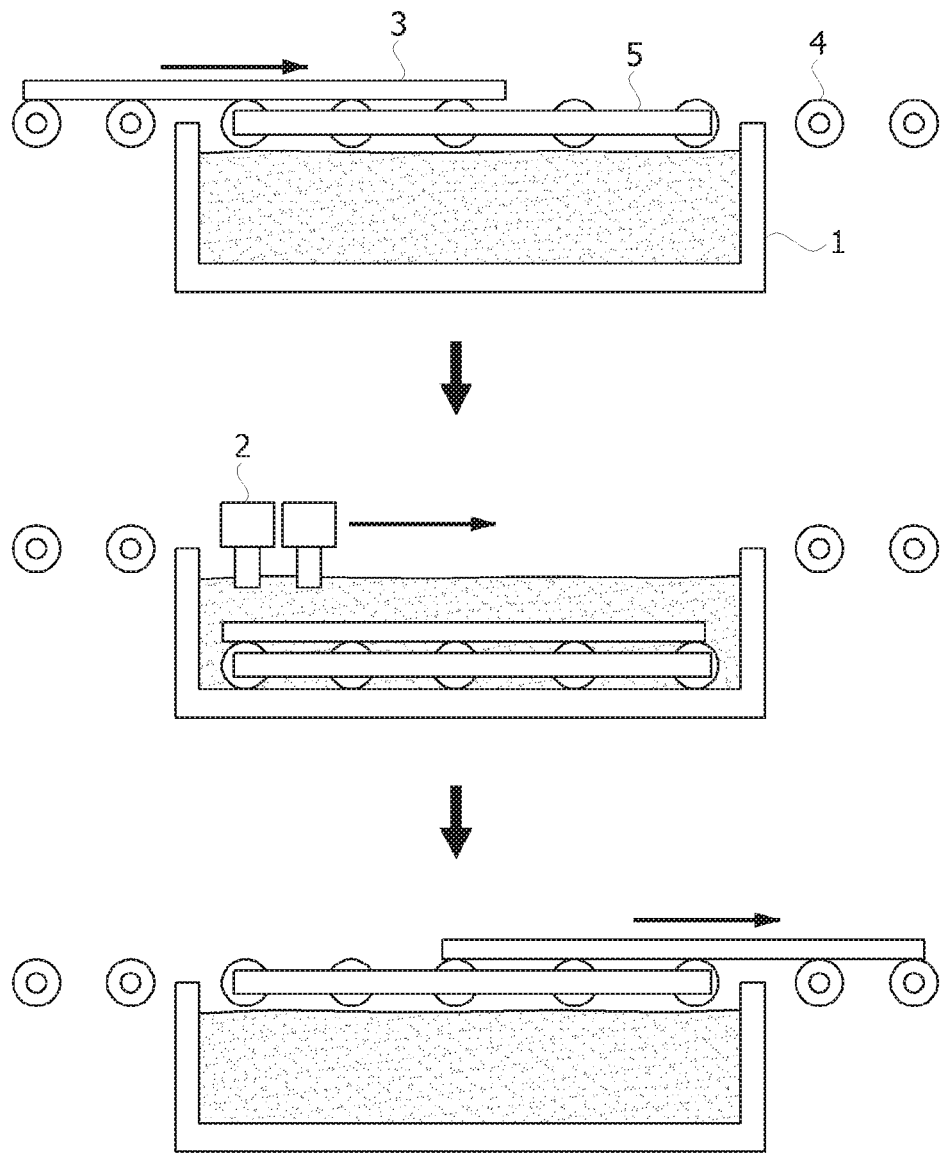
FIG. 1 is a concept view illustrating a conventional submersible ultrasonic detection method.
Figure 2:
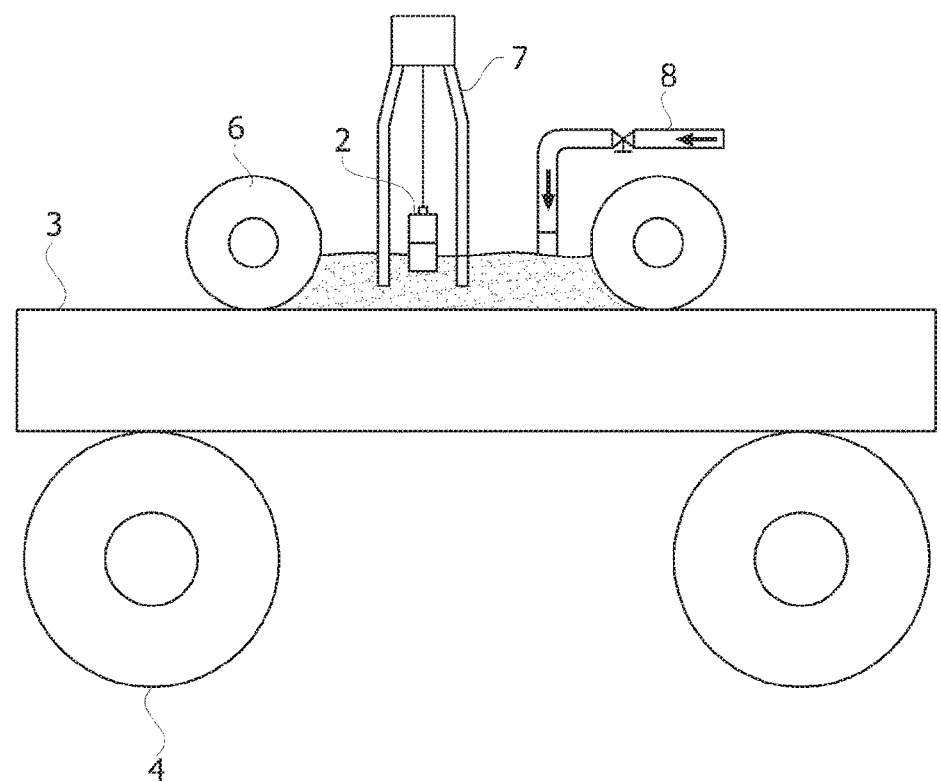
FIG. 2 is a concept view illustrating a conventional waterjet ultrasonic detection method.
Figure 3:
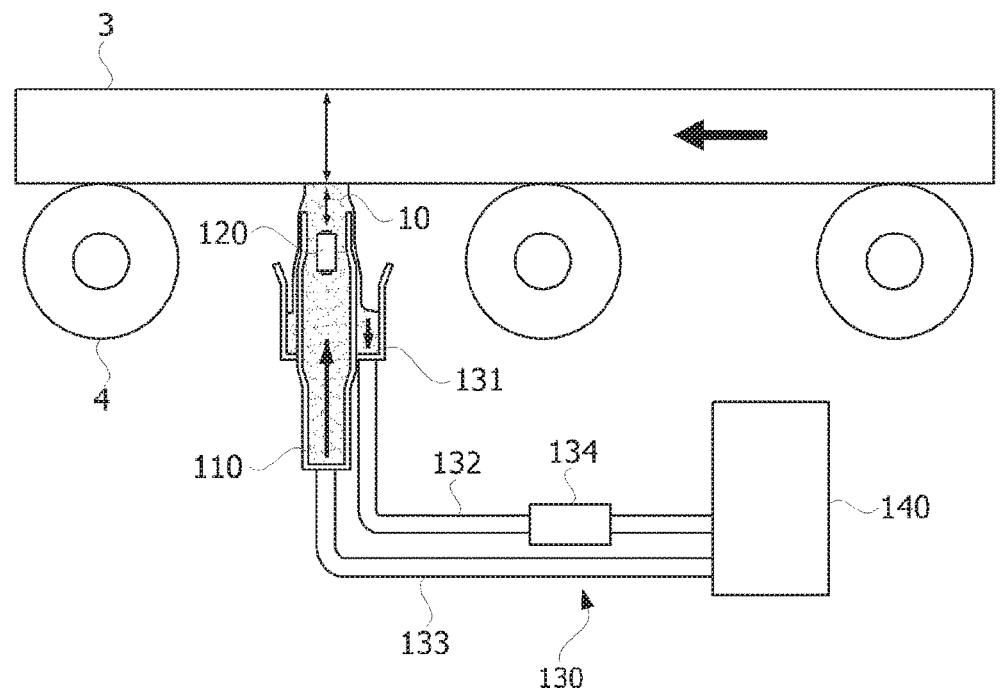
FIG. 3 is a concept view of an ultrasonic detection apparatus according to an exemplary embodiment of the present invention.

FIG. 3 is a concept view of an ultrasonic detection apparatus according to an exemplary embodiment of the present invention.

Referring to FIG. 3, the ultrasonic detection apparatus according to the embodiment of the present invention includes an injection nozzle 110, an ultrasonic probe 120, and a medium circulation unit 130.

The injection nozzle 110 is installed below a steel plate 3 transported by a transfer unit, for example, a roll 4 and jets a medium, (water for example) toward the steel plate 3 to form a medium column 10 (a column of water for example). The medium column 10 may be formed at a height of several tens mm from a jet hole of the injection nozzle 110, so that stable transmission and reception of ultrasonic waves are possible.

The ultrasonic probe 120 is installed inside the injection nozzle 110 and transmits and receives ultrasonic waves for detecting flaws of the steel plate 3 through the medium column 10. The ultrasonic probe 120 is supported by a supporting structure in the injection nozzle 110 and has a submersion type probe submersed by the medium. The ultrasonic probe 120 is connected to a data processor which processes and computes an ultrasonic signal received from the steel plate 3 and analyzes whether there is a flaw in the steel plate 3 through a wired or wireless connection method. When the wireless connection method is applied, the ultrasonic probe 120 includes a built-in wireless communications module to wirelessly transmit the ultrasonic signal to the data processor.

The medium circulation unit 130 reclaims the medium which falls from the medium column 10 and allows the medium to circulate through the injection nozzle 110. According to the embodiment, the medium circulation unit 130 includes a medium plate 131, a reclaiming pipe 132, and a supply pipe 133.

The medium plate 131 is installed on an outer perimeter of the injection nozzle 110 and is configured to receive the medium falling from the medium column 10. The medium plate 131 may be formed in a cylinder or box shape which defines the injection nozzle 110.

The reclaiming pipe 132 is connected to the medium plate 131 and is configured to reclaim the medium in the medium plate 131. The medium falling from the medium column 10 to the medium plate 131 is supplied to the reclaiming pipe 132.

A filter 134 for filtering the medium discharged from the medium plate 131 may be installed at the reclaiming pipe 132, and by this the medium with impurities removed may be supplied again to the injection nozzle 110.

The supply pipe 133 is for supplying the medium in the reclaiming pipe 132 to the injection nozzle 110 and is connected with each of the injection nozzle 110 and the reclaiming pipe 132.

The ultrasonic detection apparatus according to the embodiment may include a jet pressure control unit 140 for supplying jet pressure to the injection nozzle 110 and controlling the jet pressure of the injection nozzle 110. The jet pressure control unit 140 may be installed between the supply pipe 133 and the reclaiming pipe 132. The injection nozzle 110 jets the medium at a certain pressure according to the pressure supplied by the jet pressure control unit 140, thereby forming the medium column 10. The jet pressure control unit 140 may be a circulation pump, and the jet pressure of the injection nozzle 110 may be controlled by controlling the circulation pump.

Figure 4:
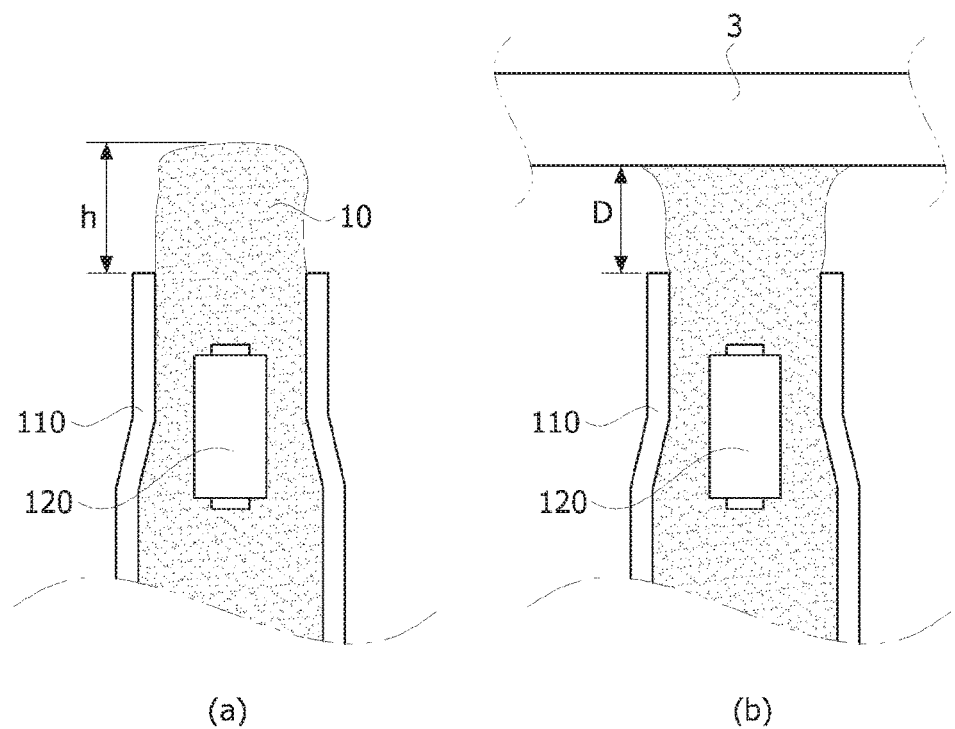
FIGS. 4A and 4B are views illustrating a method of forming a medium column using an injection nozzle shown in FIG. 3.

FIGS. 4A and 4B are views illustrating a method of forming the medium column 10 using the injection nozzle 110 shown in FIG. 3.

FIG. 4A illustrates a shape of the medium column 10 formed by the injection nozzle 110, and FIG. 4B illustrates a state in which the medium column 10 formed by the injection nozzle 110 is in contact with the steel plate 3.

As shown in FIGS. 4A and 4B, a height h of the medium column 10 may be formed to be greater than a distance D between the jet hole of the injection nozzle 110 and a lower surface of the steel plate 3. As described above, by forming the medium column 10 to have the height h greater than the distance D between the jet hole of the injection nozzle 110 and the lower surface of the steel plate 3, the medium column 10 may be closely attached to the steel plate 3, thereby forming the medium column 10 for stably transmitting and receiving ultrasonic waves.

Hereinafter, an ultrasonic detection method using the ultrasonic detection apparatus according to the embodiment will be described.

First, the steel plate 3 which is the object to be inspected for the presence of flaws is transported by a transfer unit, that is, the roll 4. Then, the medium column 10 is formed by jetting the medium to the steel plate 3 through the injection nozzle 110 installed below the steel plate 3.

Next, the ultrasonic probe 120 disposed on the injection nozzle 110 is operated to transmit and receive ultrasonic waves through the medium column, thereby detecting internal flaws of the steel plate 3. The data processor processes an ultrasonic signal transmitted from the ultrasonic probe 120 and derives a result value.

Figure 5:
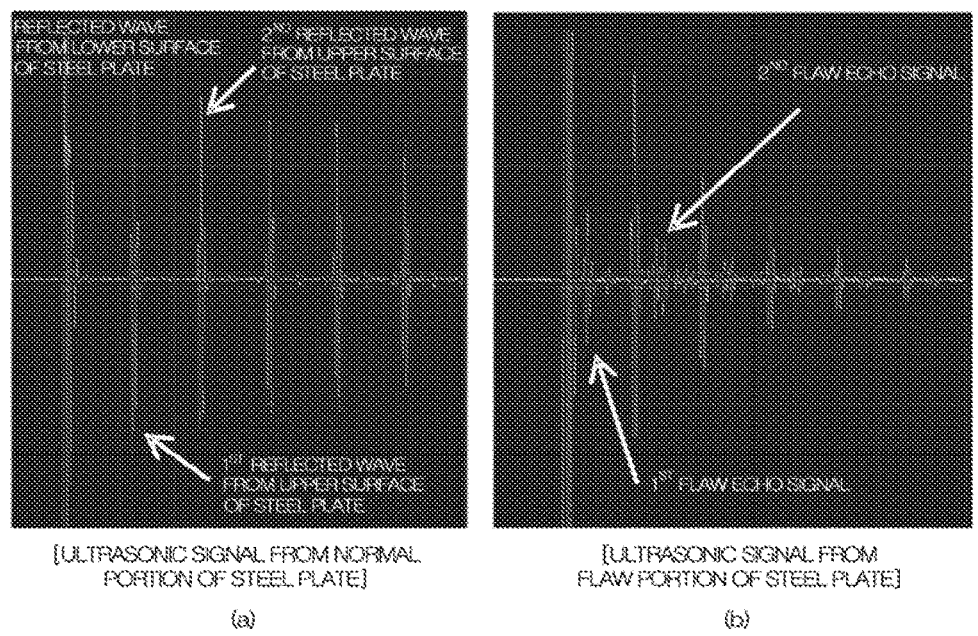
FIGS. 5A and 5B are graphs illustrating ultrasonic detection results according to an exemplary embodiment of the present invention.

FIGS. 5A and 5B illustrate results of processing ultrasonic signals related to the aforementioned. FIG. 5A illustrates a result of processing an ultrasonic signal of a steel plate with no internal flaws. FIG. 5B illustrates a result of processing an ultrasonic signal of a steel plate with internal flaws.

The medium which forms the medium column falls due to its own weight and the falling medium is reclaimed using the medium circulation unit 130 with the configuration described above and supplied again to the injection nozzle 110. Accordingly, it is possible to prevent the medium from falling to the ground, and it is unnecessary to continuously supply the medium from the outside during an ultrasonic detection process.

Meanwhile, it is possible to use a circulation pump as the jet pressure control unit 140 as described above. However, a configuration of the jet pressure control unit 140 capable of precisely controlling a jet pressure of the injection nozzle 110 will be described with reference to FIGS. 6 to 10, in comparison to the method of controlling through controlling the circulation pump.

Figure 6:
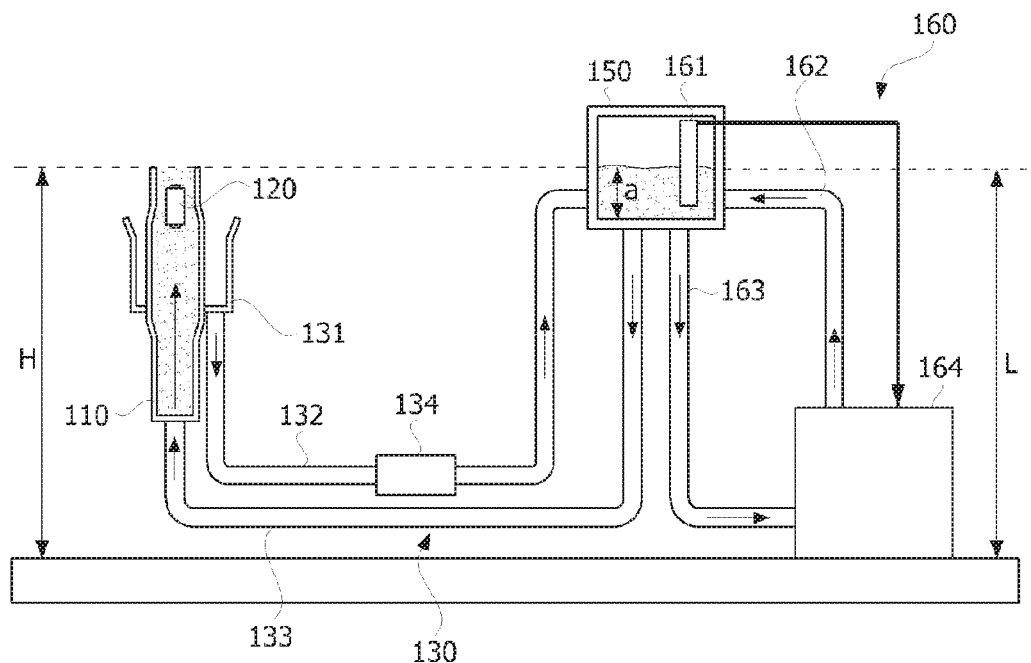
FIGS. 6 and 7 are concept views illustrating a jet pressure control unit according to an exemplary embodiment of the present invention.
Figure 7:
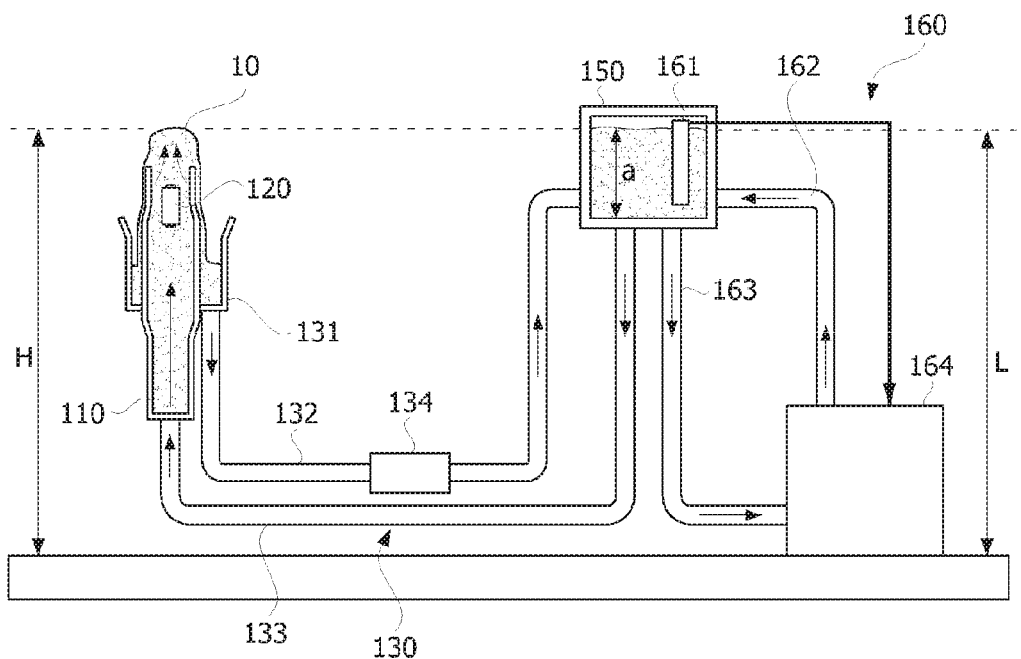

FIGS. 6 and 7 are concept views illustrating a jet pressure control unit according to an exemplary embodiment of the present invention. FIG. 6 illustrates an initial state in which a medium has not been jetted by the injection nozzle 110, and FIG. 7 illustrates a state in which the medium is being jetted by the injection nozzle 110 and the medium column 10 has been formed.

The jet pressure control unit 140 according to the embodiment includes a medium chamber 150 and a surface level adjustor 160.

The medium chamber 150 contains the medium which falls from the medium column 10 and is reclaimed and supplies the medium contained therein again to the injection nozzle 110. The medium chamber 150 may be connected to each of the reclaiming pipe 132 and the supply pipe 133 to circulate the medium. That is, the medium chamber 150 is connected to the injection nozzle 110 by the supply pipe 133 and connected to the medium plate 131 by the reclaiming pipe 132. According to a structure described above, the medium at the medium plate 131 passes through the reclaiming pipe 132 and is supplied to the medium chamber 150, and the medium in the medium chamber 150 passes through the supply pipe 133 and is supplied to the injection nozzle 110.

The surface level adjustor 160 is configured to control the jet pressure of the injection nozzle 110 by adjusting a surface level a of the medium contained in the medium chamber 150.

According to the embodiment, the surface level adjustor 160 includes a level sensor 161, first and second pipes 162 and 163, and a control unit 164.

The level sensor 161 is installed in the medium chamber 150 and senses the surface level of the medium contained in the medium chamber 150.

Each of the first and second pipes 162 and 163 is connected to the medium chamber 150. The first pipe 162 is for supplying the medium to the medium chamber 150, and the second pipe 163 is for discharging the medium from the medium chamber 150.

The control unit 164 is connected to the first and second pipes 162 and 163 and controls flow rates of the medium in the first and second pipes 162 and 163 based on a value sensed by the level sensor 161 to allow the surface level a of the medium to have a certain value. Here, the certain value is set based on a value input by a user.

Hereinafter, an operation state of the jet pressure control unit 140 according to the embodiment will be described.

According to the configuration described above, a height H from the ground to a medium end of the injection nozzle 110 always coincides with a length L from the ground and a surface of the medium in the medium chamber 150. When the surface level a of the medium in the medium chamber 150 changes, the height H of the end of the medium of the injection nozzle 110 is also changed.

As shown in FIG. 7, the length L from the ground (or an installation surface) to the surface of the medium in the medium chamber 150 becomes higher than a height from the ground (or the installation surface) to the jet hole of the injection nozzle 110, the medium is jetted from the injection nozzle 110 to start to form the medium column 10, that is, a column of water.

The control unit 164 may compare a setting value input by the user with the value sensed by the level sensor 161 and may adjust the supply of the medium to the medium chamber 150 and a discharge of the medium from the medium chamber 150, thereby controlling the surface level of the medium in the medium chamber 150. Accordingly, a height of the medium column is adjusted, thereby controlling the jet pressure.

Figure 8:
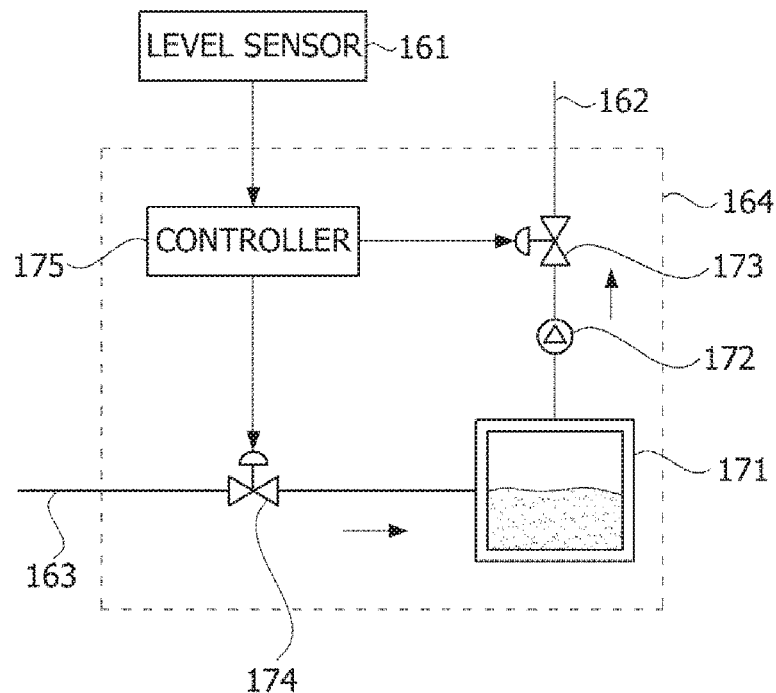
FIG. 8 is a concept view illustrating a configuration of the control unit shown in FIGS. 6 and 7.

FIG. 8 is a concept view illustrating a configuration of the control unit shown in FIGS. 6 and 7.

According to the embodiment, the control unit 164 includes a supply chamber 171, a supply pump 172, first and second control valves 173 and 174, and a controller 175.

The supply chamber 171 is connected between the first pipe 162 and the second pipe 163 and contains the medium reclaimed from the medium chamber 150 or to be supplied to the medium chamber 150.

The supply pump 172 is installed at the first pipe 162 or the second pipe 163 and provides a transport force for transporting the medium. In the embodiment, it is shown that the supply pump 172 is installed at the first pipe 162.

The first and second control valves 173 and 174 are respectively installed at the first and second pipes 162 and 163 to control opening and closing and opening rates of the first and second pipes 162 and 163. According to operations of the first and second control valves 173 and 174, the flow rates of the medium of the first and second pipes 162 and 163 are adjusted.

The controller 175 is connected to the level sensor 161 and controls the operations of the first and second control valves 173 and 174 based on the value sensed by the level sensor 161 and the setting value of the user.

The configuration of the control unit 164 described above is merely an example of various embodiments and may be provided in any form having a configuration capable of controlling the surface level a of the medium in the medium chamber 150 based on the value sensed by the level sensor 161.

Figure 9:
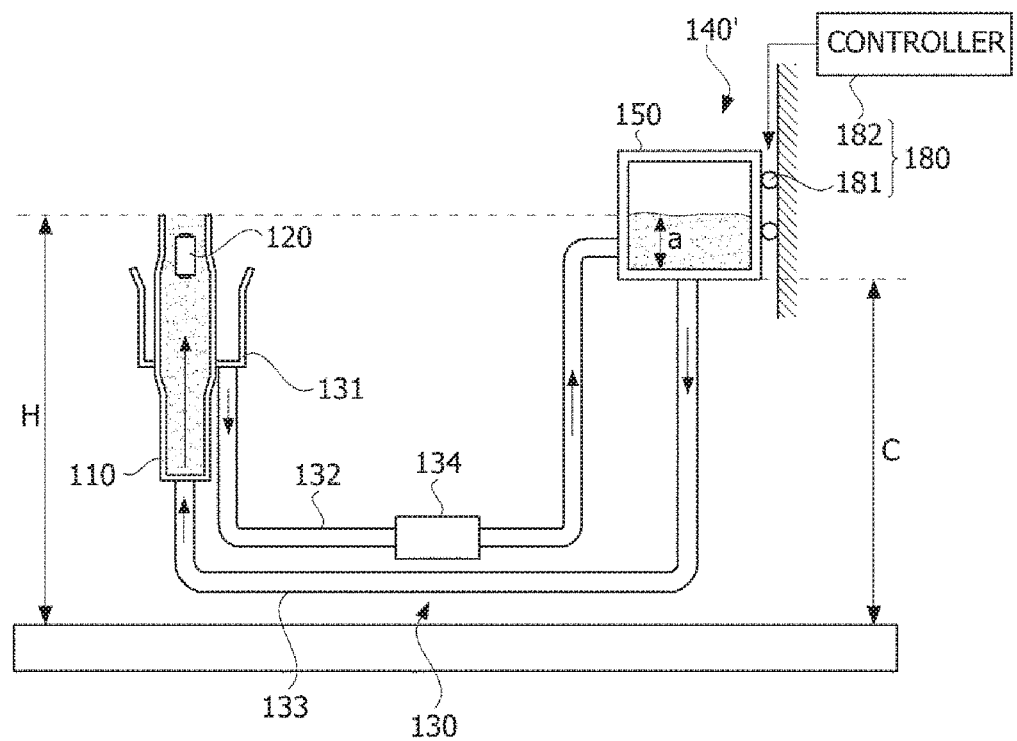
FIGS. 9 and 10 are concept views illustrating a jet pressure control unit according to another exemplary embodiment of the present invention.
Figure 10:
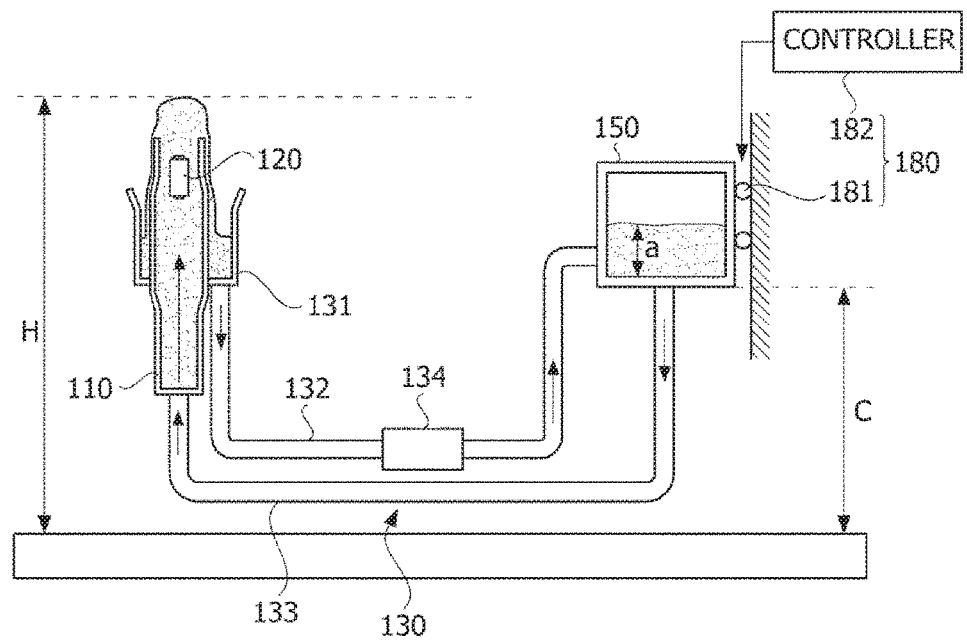

FIGS. 9 and 10 are concept views illustrating a jet pressure control unit according to another exemplary embodiment of the present invention. FIG. 9 illustrates an initial state in which a medium has not been jetted by the injection nozzle 110, and FIG. 10 illustrates a state in which the medium is being jetted by the injection nozzle 110 and the medium column 10 has been formed.

A jet pressure control unit 140' according to the embodiment includes the medium chamber 150 and a chamber height adjustor 180.

Since the medium chamber 150 has the same configuration as that in the previous embodiment, a description thereof will be omitted.

However, in the embodiment, the medium chamber 150 is configured vertically movable. A guide structure which guides a vertical movement of the medium chamber 150 may be provided between the medium chamber 150 and a supporting structure. Also, to allow the medium chamber 150 to vertically move, the supply pipe 133 and the reclaiming pipe 132 may have a flexible material or may be configured to relatively move with respect to the medium chamber 150.

The chamber height adjustor 180 is configured to control a jet pressure of the injection nozzle 110 by adjusting a height C of the medium chamber 150.

According to the embodiment, the chamber height adjustor 180 includes a driving portion 181 and a controller 182.

The driving portion 181 is for driving the medium chamber 150 in the vertical direction and may be formed of various components including a linear motor, a ball-screw, a rack and pinion, etc.

The controller 182 is configured to control an operation of the driving portion 181 according to an input signal. For example, the operation of the driving portion 181 may be controlled based on a value input by a user so that the medium chamber 150 is located at a position set by the user.

Describing an operation state of the jet pressure control unit 140' according to the embodiment, only circulation of the medium occurs between the injection nozzle 110 and the medium chamber 150, and an input or output of the medium into or from the circulation system does not occur. Accordingly, when a change occurs in the height of the medium chamber 150, no change occurs in the surface level of the medium in the medium chamber 150, and only the height H from the ground to an end of the medium of the injection nozzle 110 is changed.

In the embodiment, using the above described, when a position of the medium chamber 150 is moved up to a certain height from the initial state shown in FIG. 9 to the state shown in FIG. 10, the medium is jetted by the injection nozzle 110 and forms the medium column 10. Since the controller 182 may adjust the height of the medium chamber 150 by controlling the operation of the driving portion 181, a height of the medium column 10 is adjusted, thereby making it possible to control the jet pressure.

Figure 11:
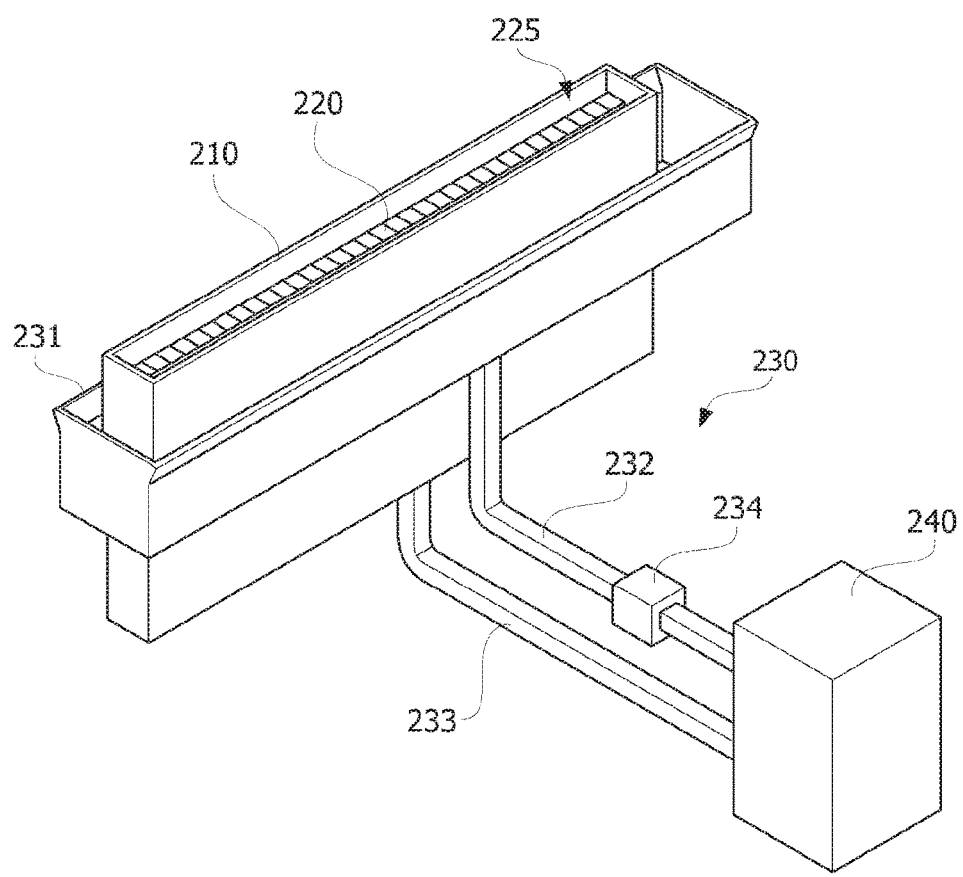
FIG. 11 is a perspective view of an ultrasonic detection apparatus according to another exemplary embodiment of the present invention.
Figure 12:
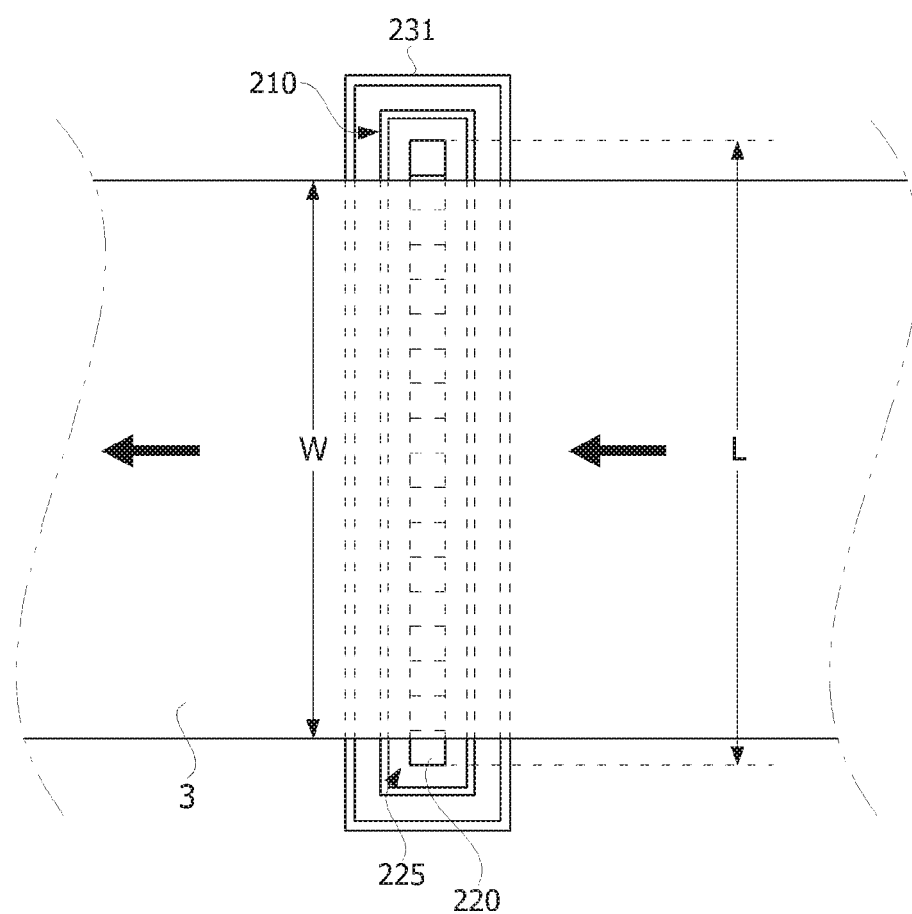
FIG. 12 is a plan view of the ultrasonic detection apparatus shown in FIG. 11.

FIG. 11 is a perspective view of an ultrasonic detection apparatus according to another exemplary embodiment of the present invention. FIG. 12 is a plan view of the ultrasonic detection apparatus shown in FIG. 11.

Like the previous embodiment, the ultrasonic detection apparatus according to the embodiment includes an injection nozzle 210, an ultrasonic probe 220, a medium circulation unit 230, a jet pressure supply unit 240, etc.

In FIGS. 11 and 12, reference numerals designate elements that correspond to elements of the earlier embodiment are assigned similarly as in the earlier embodiment. That is, reference numerals shown in 100s in the previous embodiment are changed in 200s.

According to the embodiment, a plurality of ultrasonic probes 220 are arranged in the width direction of the steel plate 3 and form a probe array 225. Here, the probe array 225 may have a length L that is greater than or equal to a width W of the steel plate 3.

The injection nozzle 210 is formed to accommodate the probe array 225. In the embodiment, it is shown that the injection nozzle 210 has a quadrangular cross section with the width direction of the steel plate 3 as the longitudinal direction. Also, it is shown that a medium plate 231 also has a quadrangular box shape which defines an outer perimeter of the injection nozzle 210. However, the shapes of the injection nozzle 210 and the medium plate 231 according to the embodiment are not limited to the aforementioned and may be modified in various shapes.

According to the embodiment, since the plurality of probes 220 arranged in the width direction of the steel plate 3 cover the full width of the steel plate 3, there is an advantage where it is possible to detect the full width of the steel plate 3 at the same time while the steel plate 3 is being transported.

The apparatus and method for ultrasonic detection to detect flaws in a steel plate described above are not limited to the configurations and method described above. All or some of the embodiments may be selectively combined and configured to perform various modifications. Also, the various modifications may be executed by one of ordinary skill in the art within the technical scope of the present invention.

According to the embodiments of the present invention, ultrasonic waves are transmitted and received through a medium column formed below a steel plate, thereby stably transmitting and receiving ultrasonic waves with no contact.

Also, since a medium circulation unit is provided to reuse a medium which falls from a medium column, the medium is prevented from falling to the ground, and it is unnecessary to continually supply an ultrasonic detection type medium.

Also, since it is possible to precisely control a jet pressure of an injection nozzle by adjusting the height of a surface of a medium in a medium chamber or adjusting the height of the medium chamber, the occurrence of a torrent and a pulsation is prevented in the medium column, thereby forming a stable medium column.

Also, it is possible to detect a full length of a steel plate. When an ultrasonic probe is formed in an array shape, it is possible to detect the full width of the steel plate at the same time.

While the invention has been shown and described with reference to certain exemplary embodiments thereof, it will be understood by those skilled in the art that various changes in form and details may be made therein without departing from the spirit and scope of the invention as defined by the appended claims.

What is claimed is:

1. An ultrasonic detection apparatus comprising:
   an injection nozzle which is installed below a steel plate being transported and configured to form a medium column by jetting a medium toward the steel plate;
   an ultrasonic probe which is installed in the injection nozzle and configured to transmit and receive ultrasonic waves for detecting flaws in the steel plate through the medium column;
   a medium circulation unit which reclaims the medium falling from the medium column and circulates the reclaimed medium to the injection nozzle; and
   a jet pressure control unit for supplying a jet pressure to the injection nozzle and controlling the jet pressure of the injection nozzle,
   wherein the jet pressure control unit comprises:
      a medium chamber for containing the medium which falls from the medium column and is reclaimed and supplying the contained medium again to the injection nozzle, and
      a chamber height adjustor which is configured to adjust a height of the medium chamber to control the jet pressure of the injection nozzle.

2. The ultrasonic detection apparatus of claim 1, wherein the medium circulation unit comprises:
   a medium plate which is installed on an outer perimeter of the injection nozzle and configured to receive the medium which falls from the medium column;
   a reclaiming pipe which is connected to the medium plate and configured to reclaim the medium in the medium plate; and
   a supply pipe for supplying the medium in the reclaiming pipe to the injection nozzle.

3. The ultrasonic detection apparatus of claim 2, wherein a filter for filtering the medium discharged from the medium plate is installed at the reclaiming pipe.

4. The ultrasonic detection apparatus of claim 2, wherein the jet pressure control unit is installed between the supply pipe connected to the injection nozzle and the reclaiming pipe connected to the medium plate installed on the outer perimeter of the injection nozzle.

5. The ultrasonic detection apparatus of claim 1, wherein the jet pressure control unit is a circulation pump.

6. The ultrasonic detection apparatus of claim 1, wherein the jet pressure control unit comprises:
   a medium chamber for containing the medium which falls from the medium column and is reclaimed and supplying the contained medium again to the injection nozzle; and
   a surface level adjustor which is configured to adjust the surface level of the medium contained in the medium chamber to control the jet pressure of the injection nozzle.

7. The ultrasonic detection apparatus of claim 6, wherein the surface level adjustor comprises:
   a level sensor which is configured to sense the surface level of the medium contained in the medium chamber;
   a first pipe for supplying the medium to the medium chamber;
   a second pipe for discharging the medium from the medium chamber; and
   a control unit which is connected to the first and second pipes and configured to control flow rates of the medium in the first and second pipes such that the surface level of the medium has a certain value based on a value sensed by the level sensor.

8. The ultrasonic detection apparatus of claim 7, wherein the control unit comprises:
   a supply chamber which is connected between the first and second pipes and contains the medium;
   a supply pump installed at one of the first pipe and the second pipe;
   first and second control valves installed at the first and second pipes, respectively; and
   a controller which is configured to control the first and second control valves based on the value sensed by the level sensor.

9. The ultrasonic detection apparatus of claim 1, wherein the chamber height adjustor comprises:
   a driving portion which is configured to drive the medium chamber to move in the vertical direction; and
   a controller which is configured to control an operation of the driving portion according to an input signal.

10. The ultrasonic detection apparatus of claim 1, wherein a plurality of such ultrasonic probes are arranged in the width direction of the steel plate, and
   wherein the injection nozzle is configured to accommodate a probe array formed by the plurality of ultrasonic probes.

11. The ultrasonic detection apparatus of claim 10, wherein the probe array has a length that is greater than or equal to the width of the steel plate.

* * * * *